United States Patent
Darwin et al.

(10) Patent No.: US 9,125,403 B2
(45) Date of Patent: Sep. 8, 2015

(54) WATERPROOFING AND PRESERVATIVE COMPOSITIONS FOR ORGANIC MATERIAL

(71) Applicants: David C. Darwin, Wayne, NJ (US); Philip S. Rhodes, Teaneck, NJ (US); Jason S. Tuerack, Jericho, NY (US)

(72) Inventors: David C. Darwin, Wayne, NJ (US); Philip S. Rhodes, Teaneck, NJ (US); Jason S. Tuerack, Jericho, NY (US)

(73) Assignee: Hycrete, Inc., Carlstadt, NJ (US)

( * ) Notice: Subject to any disclaimer, the term of this patent is extended or adjusted under 35 U.S.C. 154(b) by 246 days.

(21) Appl. No.: 13/855,993

(22) Filed: Apr. 3, 2013

(65) Prior Publication Data

US 2013/0337280 A1 Dec. 19, 2013

Related U.S. Application Data

(60) Provisional application No. 61/660,066, filed on Jun. 15, 2012.

(51) Int. Cl.
*A01N 37/06* (2006.01)
*B27K 3/34* (2006.01)

(52) U.S. Cl.
CPC . *A01N 37/06* (2013.01); *B27K 3/34* (2013.01); *Y10T 428/662* (2015.04)

(58) Field of Classification Search
CPC ............ A01N 37/06; B27K 3/34; B27K 3/36; B27K 3/50; B27K 3/52
USPC ....................... 106/2, 15.05; 428/537.1, 537.5
See application file for complete search history.

(56) References Cited

U.S. PATENT DOCUMENTS

| | | |
|---|---|---|
| 5,486,231 A | 1/1996 | Dulaney |
| 7,261,923 B2 | 8/2007 | Rhodes et al. |
| 7,264,886 B2 | 9/2007 | Cui et al. |
| 7,381,252 B2 | 6/2008 | Rhodes et al. |
| 7,407,535 B1 | 8/2008 | Humphrey et al. |
| 7,498,090 B2 | 3/2009 | Rhodes et al. |
| 7,513,948 B1 | 4/2009 | Humphrey et al. |
| 7,666,254 B1 | 2/2010 | Romero Amaya et al. |
| 7,670,415 B1 | 3/2010 | Rosenberg et al. |
| 7,790,239 B2 | 9/2010 | Magnee et al. |
| RE42,384 E | 5/2011 | Humphrey et al. |
| 7,935,182 B2 | 5/2011 | Humar et al. |
| 7,959,723 B2 | 6/2011 | Bigorra Llosas et al. |
| 2010/0196723 A1 | 8/2010 | Veramallay et al. |

FOREIGN PATENT DOCUMENTS

EP  0439369 A1 * 7/1991

OTHER PUBLICATIONS

Chemical Abstract Accession No. 1981:71225 (Document No. 94:71225), abstract of German Patent Specification No. DE 2915948 A1 (Nov. 1980).*
Chemical Abstract Accession No. 1983:541820 (Document No. 99:141820), abstract of German Patent Specification No. DE 3300438 A1 (Jul. 1983).*

* cited by examiner

*Primary Examiner* — Anthony J Green
(74) *Attorney, Agent, or Firm* — McCarter & English, LLP

(57) ABSTRACT

Compositions, kits and methods using a cationic salt of a dioic acid to treat organic material, including wood and wood-containing material, are disclosed. The treatment may be supplemented with a second salt. Reductions in the rate and/or impact of water absorption, dimensional instability and living organism decay are achieved for organic materials.

21 Claims, No Drawings

WATERPROOFING AND PRESERVATIVE COMPOSITIONS FOR ORGANIC MATERIAL

CROSS REFERENCE TO RELATED APPLICATIONS

This application claims priority to U.S. Provisional Application Ser. No. 61/660,066, filed Jun. 15, 2012, the entirety of which is incorporated by reference herein.

BACKGROUND OF THE INVENTION

1. Technical Field

The present disclosure generally relates to compositions, kits and methods for use with organic material (e.g., wood and wood-containing material) that are subject to environmental damage and, more particularly, relates to compositions, kits and methods using a cationic salt of a dioic acid to improve hydrophobicity, dimensional stability and bioresistance of organic material.

2. Description of Background Art

Organic materials, such as wood, are basic and common construction materials. As a renewable resource, organic materials are likely to remain a prime staple of construction. Organic materials, such as wood, however are susceptible to deterioration from environmental conditions. Water absorption and living organism decay are two major driving forces behind organic material deterioration.

In the case of wood, water absorption occurs when water penetrates the wood surface and/or enters into the pores of the wood. Water penetration damages wood and may also bring deleterious substances into the pores. Water absorption causes wood to swell. Likewise, water desorption may cause wood to shrink. The resistance of wood to swelling, or shrinking, as a function of water content is related to its dimensional stability. In general, the dimensional stability of untreated wood is poor. A lack of dimensional stability leads to warping and splitting. Since most wood is painted, coated or impregnated, as wood warps any paint or stain finish is damaged. As a result, dimensionally unstable wood must be recoated or replaced with a substitute.

Wood may also be damaged by living organism decay. For example, termites and fungal rot consume wood causing loss of wood structure. Such organisms destroy the desirable structural stability imparted by the cellulosic cell wall microstructures of wood.

Efforts have been made to prevent environmental deterioration of organic materials, such as wood and wood-containing materials. Most often, chemical compositions have been investigated to protect wood from water absorption and living organism decay. These chemical compositions are primarily administered by impregnating the compositions into the wood pores via a pressure treatment process involving soaking wood in the chemical solution under pressures up to 150 psi.

For example, U.S. Pat. No. 7,264,886 describes a wax emulsion water repellent composition that includes wax, a nonionic surfactant, an anionic surfactant and water for waterproofing wood. U.S. Pat. No. 5,486,231 describes a water repellent solution for wood that includes an organometallic complex of a hydrophobic fatty acid coordinated with a halogenated trivalent chromium and water. U.S. Pat. No. 7,959,723 describes compositions that include biocides and dialkylamides for the protection of wood from living organism decay. U.S. Pat. No. 7,935,182 describes a solution that includes amines, copper salts, boron salts, carboxylic acids and selected quaternary ammonium biocides which also prevent living organism decay in wood. U.S. Pat. No. 7,666,254 describes the use of a boron compound and bifenthrin to protect wood from termite attack.

Acetylation is another known technique used to treat wood. In acetylation, acetic anhydride is pressure treated into the wood. During acetylation, an acetyl group is grafted onto a free hydroxyl group on the wood cellulose under heated conditions at temperatures up to 140° C. Acetylation may provide wood with some dimensional stability and living organism decay resistance, but provides limited water absorption protection. Acetylation also produces concentrated acetic acid in the wood pores giving the wood an unpleasant vinegar odor. The acetic acid must be removed prior to use. To do so requires post reaction processing using large scale pressure treatment plants. Similar techniques, such as those developed by Lapeyre, e.g. U.S. Pat. No. 7,790,239, use mixed anhydrides and suffer from similar limitations.

While the efforts described above provide some level of protection, none provide a desired and/or effective combination of water absorption resistance, living organism decay resistance and dimensional stability, nor do they provide such protection in water soluble, environmentally safe and easy to administer composition(s) and/or kit(s). For example, some compositions contain waxes and fatty acids that are hydrophobic. Others contain borates, copper and other chemicals that are not environmentally friendly. These materials, especially borates, may also leach out of the organic material over time.

Accordingly, despite efforts to date, a need remains for environmental-resistant treatments, materials and processes for organic materials, such as wood and wood-containing materials, that are effective, efficient and reliable. These and other needs are advantageously satisfied by the disclosed compositions, kits and methods for water absorption resistance, living organism decay resistance, and dimensional stability of organic materials. These advantages have been achieved with water-based solutions that do not require specialized acid-resistant pressure treatment equipment or large scale pressure treatment plants.

SUMMARY OF THE PRESENT DISCLOSURE

It has been found that the treatment of organic material with a cationic salt of a dioic acid can advantageously enhance the durability of the organic material by providing reduced water absorption and live organism decay, as well as increased dimensional stability. It has further been found that a subsequent treatment of the organic material treated with the cationic salt of a dioic acid with a second water soluble salt solution results in a greater effectiveness of the waterproofing and bioresistance.

According to the present disclosure, compositions, kits and methods for use in treating organic material and surfaces are provided. In one embodiment, the present disclosure relates to a composition including an organic material and an active ingredient of formula [I]

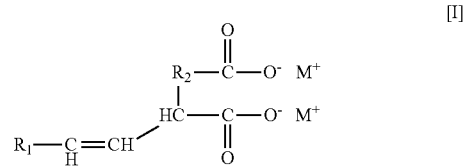

wherein $R_1$ is an aliphatic hydrocarbon, $R_2$ is a $C_1$ to $C_{10}$ hydrocarbon, and each $M^+$ is independently a cation. The active ingredient may have a blend or mixture of molecules having differing $R_1$ structures. The composition may further include a second salt.

The composition, kit and method of the present disclosure is applicable to all organic and organic-containing material, including wood, paper and natural textile fibers.

In another embodiment, the present disclosure relates to a kit including a first component being an active ingredient of formula [I] and a second component being a salt.

In yet another embodiment, the present disclosure relates to a method to treating organic material that includes the steps of providing a composition having an active ingredient of formula [I] and applying the composition to the organic material. The method may further include the step of applying a second composition including a second salt to the organic material.

Additional features, functionalities and beneficial results associated with the disclosed solution/system and treatment modalities associated therewith will be apparent from the detailed description which follows.

DETAILED DESCRIPTION OF EXEMPLARY EMBODIMENT(S)

The present disclosure relates to compositions, kits and methods using a cationic salt of a dioic acid to treat organic or organic-containing materials. The treatment may be supplemented by subsequent treatment of the organic or organic-containing material with a second salt solution. The treatment is effective in reducing the rate and/or impact of water absorption, dimensional instability and living organism decay on organic or organic-containing materials.

As used herein the term "water absorption" refers to the capacity of organic or organic-containing materials, such as wood, to absorb water. Absorption can be measured by weight gain.

As used herein the term "hydrophobicity" refers to the repellency of water, for example, by non-polar organic chain molecular structures.

As used herein the term "dimensional stability" refers to the ability of an organic or an organic-containing materials, such as wood, to resist change volume upon water exposure, for example, wood volume expansion upon absorbing water and wood volume contraction upon drying.

As used herein the term "warping" refers to a deviation from flatness in the organic or organic-containing material, such as wood, as a result of the absorption and/or desorption of water.

As used herein the term "living organism decay" refers to degradation of physical properties of an organic or organic-containing material by attack from insects and microorganisms, for example, mass loss of wood due to insect consumption or strength loss of wood due to fungal decay of the wood molecular structure.

As used herein the term "bioresistance" refers to the ability to retard living organism decay.

The disclosed compositions, kits and methods advantageously deliver integral waterproofing that may render organic or organic-containing materials essentially hydrophobic. As described herein, treatment with the disclosed compositions, kits and methods advantageously transforms organic or organic-containing materials from an open network of microstructure and capillaries into a structure that exhibits ultra-low absorption characteristics, thereby effecting a desirable level of waterproofing.

Without wishing to be bound by any theory, it is believed that the cationic salt of a dioic acid disclosed herein is able to interact with the microstructure and capillaries to form occlusions within the microstructure. Subsequent treatment with a second salt solution, such as calcium nitrite, causes irreversible precipitation or polymerization of the dioic acid within the microstructure.

In one embodiment, the present disclosure relates to a composition including an organic or an organic-containing material, and an active ingredient of formula [I]

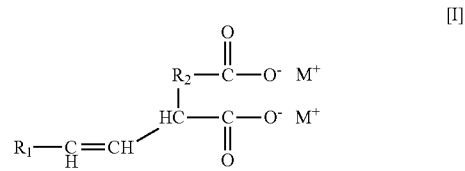

[I]

wherein $R_1$ is an aliphatic hydrocarbon, $R_2$ is a $C_1$ to $C_{10}$ hydrocarbon, and each $M^+$ is independently a cation.

The organic or organic-containing materials may be any wood or wood-containing material or natural textile fiber or fiber-containing material subject to environmental deterioration by water absorption or live organism decay. The wood or wood-containing material may include, but is not limited to, hardwood, softwood, cellulose-based materials and composite materials. Examples of suitable hardwood are oak, maple, cherry, birch, ash, popular and teak. Examples of suitable softwood are pine, hemlock, fir, redwood, spruce and cedar. Examples of suitable cellulose-based materials are paper, paper products and cardboard. Examples of suitable composite materials are plywood, fiberboard and wood-plastic composites. The wood or wood-containing material may also including building and construction products, such as fencing, siding, decking, window frames, sills, doors, trim board, posts, railroad ties and telephone/electrical poles. The wood or wood-containing material may also include a treated veneer on the surface of a wood or non-wood core material.

The natural textile fiber or fiber-containing material may include, but is not limited to, animal and plant fibers. Examples of suitable animal fibers are silk, wool, angora, cashmere and mohair. Examples of suitable plant fibers are cotton, linen, rayon, hemp and jute.

The hydrocarbon group denoted as $R_1$ in the active ingredient may either be branched or linear. In preferred embodiments, $R_1$ may include $C_6$ to $C_{22}$ hydrocarbons, $C_8$ to $C_{16}$ hydrocarbons, $C_{10}$ to $C_{14}$ hydrocarbons, and $C_{12}$ hydrocarbons.

In some embodiments, the active ingredient may have a blend or mixture of molecules having differing $R_1$ structures. The precise chemical formula of the molecules included in the blend or mixture may be non-uniform. Thus, in an exemplary blend or mixture, a percentage of the molecules may be characterized by $R_1=C_9$, a percentage of the molecules may be characterized by $R_1=C_{10}$, and a percentage of the molecules may be characterized by $R_1=C_{11}$, etc. On a weighted basis, the average $R_1$ hydrocarbon chain length may be in the range of about a $C_8$ to about a $C_{16}$ hydrocarbon, preferably about a $C_{10}$ to about a $C_{14}$ hydrocarbon, and more preferably about a $C_{12}$ hydrocarbon. The blend or mixture of molecules may be linear, branched or a mixture thereof. In another exemplary blend or mixture, all of the molecules are characterized by having the same number of carbons, e.g. C12, which may be branched, linear, or a mixture thereof.

In one embodiment, all or substantially all of the branched hydrocarbons in the blend or mixture of $R_1$ may be a $C_8$ to $C_{16}$ hydrocarbon.

The hydrocarbon group denoted as $R_2$ in the active ingredient may include a $C_1$ to $C_{10}$ hydrocarbon, preferably a $C_1$ to $C_2$ hydrocarbon, and more preferably $R_2$ may be a $C_1$ hydrocarbon.

The cationic salt denoted as $M^+$ in the active ingredient may each independently be a monovalent metal salt, such as an alkali metal, or other monovalent cations, such as ammonium and quaternary amines. The metal salts may be selected from the group consisting of sodium, lithium and potassium. In one embodiment, each cation is a metal salt. In another embodiment, each cation is sodium.

In one embodiment, $R_1$ or the weighted average of the blend or mixture of $R_1$, is a branched $C_{12}$ hydrocarbon, $R_2$ is a $C_1$ hydrocarbon, and each $M^+$ is sodium. In another embodiment, $R_1$ is a linear $C_8$ hydrocarbon, $R_2$ is a $C_1$ hydrocarbon, and each $M^+$ is sodium.

The amount of active ingredient present in the organic or organic-containing composition is an amount sufficient to reduce water absorption of the organic or organic-containing material, increase dimensional stability of the organic or organic-containing material, preserve the organic or organic-containing material, or combinations thereof. The amount of active ingredient in the organic or organic-containing material, such as wood or wood-containing material, is about 50 weight percent to about 0.1 weight percent. Preferably, the amount of active ingredient is about 40 weight percent to about 0.5 weight percent. More preferably, the amount of active ingredient is about 30 weight percent to about 1 weight percent.

Commonly assigned U.S. RE42,384; U.S. Pat. No. 7,670,415; U.S. Pat. No. 7,513,948; U.S. Pat. No. 7,498,090; U.S. Pat. No. 7,407,535; U.S. Pat. No. 7,381,252; U.S. Pat. No. 7,261,923 and U.S. 2010/0196723 describe related active molecules, used alone or in combination with other ingredients, for waterproofing and inhibiting corrosion in concrete and concrete-related materials. Each of the aforementioned commonly assigned patents and publications is incorporated herein by reference in its entirety.

An advantageous technique for synthesizing the disclosed compositions, kits and methods involves a multi-stage process. In a first stage, a feed stream is fed to a first reaction chamber. An exemplary feed stream for synthesis of the disclosed materials, compositions and systems is characterized as follows:

A mixture/blend of unsaturated branched $C_8$ to $C_{16}$ hydrocarbon molecules;

Non-homogeneous branching;

Non-homogeneous double/triple bond locations;

An overall absence of cyclic molecules; and

A weighted average of hydrocarbon chain lengths that generally corresponds to about $C_{12}$.

Feed streams satisfying the foregoing specifications may be sourced from conventional chemical supply sources, as will be apparent to persons skilled in the art.

The foregoing feed stream is generally fed to a reactor for reaction with a maleic anhydride (2,5-furandione) of general formula:

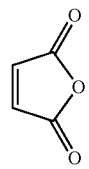

The unsaturated feed stream reacts with the maleic anhydride (in a liquefied/molten form) through an addition reaction until such time as the maleic anhydride is consumed. Reaction conditions generally involve an elevated temperature of about 400° F. to about 430° F. and an elevated pressure of about 30-40 psi. The foregoing addition reaction forms an addition compound of the following formula:

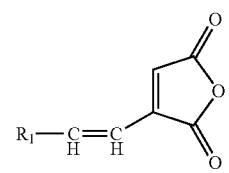

wherein $R_1$ is a $C_8$ to $C_{16}$ branched hydrocarbon.

The addition compound is generally separated from the unreacted feedstock and undesired by-products through vacuum distillation. According to exemplary processing implementations, a two pass vacuum distillation is employed (although single stage separation may be employed through appropriate separation techniques). In a first pass, unreacted feed stream constituents are flashed off at temperatures of about 350° F. In the second pass, the addition product is flashed at temperatures of about 450° F. The addition product is typically yellow in color. Residual byproducts, e.g., tars and the like, are typically discarded and/or reclaimed.

In a next reaction stage, the addition compound is generally reacted with deionized water at an elevated temperature, e.g., at or about the boiling point of water, to form a diacid. By such reaction, a diacid of general formula is formed:

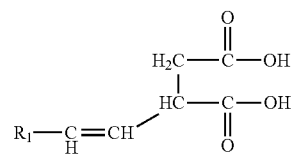

wherein $R_1$ is a $C_8$ to $C_{16}$ branched hydrocarbon. The diacid product formed by the foregoing reaction is generally a resinous solid that is soluble in water.

In the next synthesis stage, the diacid is reacted with a caustic solution that includes both sodium hydroxide and potassium hydroxide. In an exemplary embodiment, both hydroxides are supplied as aqueous solutions to a reaction chamber, e.g., at weight percentages of about 25% (with deionized water). The caustic solution generally includes sodium hydroxide at a 90 to 95 weight percentage and potassium hydroxide at a 5 to 10 weight percentage. The reaction vessel is typically closed and sufficient headroom is maintained to allow controlled pressure buildup during the reaction process. As the diacid reacts with the caustic solution, an intermediate product is generally formed of the following formula:

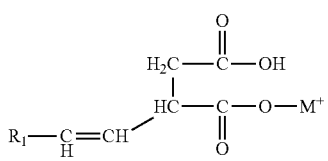

Further reaction with caustic solution yields a salt of general formula:

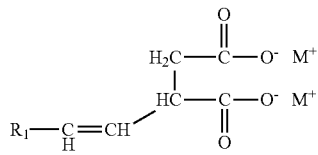

wherein $R_1$ is a $C_8$ to $C_{16}$ branched hydrocarbon and $M^+$ is $Na^+$ or $K^+$ (or one of each). pH conditions within the reaction chamber are generally monitored and the reaction is complete when the pH reaches a neutral condition, thereby evidencing depletion of the caustic solution. The salt is generally soluble in water and defines the active ingredient for purposes of the disclosed material, composition and system.

According to exemplary embodiments of the present disclosure, utilization of both sodium hydroxide and potassium hydroxide has been found to be advantageous to minimize the likelihood that the active ingredient will aggregate and precipitate from an aqueous solution. The active ingredient is generally supplied as an aqueous solution, e.g., 20% by weight active ingredient (with deionized water). In some embodiments, the interspersion of different metals has been found to significantly decrease the potential for undesirable precipitation of the active ingredient from the aqueous solution. Thus, the active compositions, kits and methods disclosed herein are water soluble and are generally stored, distributed and utilized in an aqueous form. Despite the solubility of the active ingredients/compositions disclosed herein, such ingredients/compositions are effective to inhibit and/or prevent water deterioration in organic or organic-containing materials.

The organic or organic-containing material composition of the present disclosure may further include a second salt. The amount of cation from the second salt present in the organic or organic-containing material composition is an amount sufficient to, in combination with the active ingredient, reduce water absorption of the organic or organic-containing material, increase dimensional stability of the organic or organic-containing material, preserve the organic or organic-containing material, or combinations thereof. The amount of cation from the second salt in the organic or organic-containing material is about 10 weight percent to about 0.01 weight percent. Preferably, the amount is about 5 weight percent to about 0.05 weight percent. More preferably, the amount is about 1 weight percent to about 0.1 weight percent.

In another embodiment, the present disclosure relates to a kit including components useful for waterproofing and/or rendering bioresistant organic or organic-containing materials. The kit includes a first component being an active ingredient of formula [I] as described in the present disclosure and a second component being a salt. The salt may include, but is not limited to, calcium salts, copper salts, iron salts, zinc salts, magnesium salts, aluminum salts, titanium salts and tungsten salts. Examples of suitable calcium salts include calcium nitrite, calcium nitrate, calcium acetate, calcium oxide, calcium hydroxide, calcium sulfate, calcium phosphate, calcium carbonate, calcium chloride, and mixtures thereof. Examples of suitable copper salts include copper nitrite, copper nitrate, copper hydroxide, copper oxide, copper chloride and copper sulfate.

The active ingredient and second salt may be supplied in a kit as solids, preconcentrates or solutions. For example, the active ingredient and/or salt may be supplied separately as aqueous solutions. The active ingredient aqueous solution may range from a 70% to a 0.1% solution. The second salt solution may range from a 10% to a 50% solution.

The relative amount of each component in the kit is an amount sufficient to waterproof and/or impart bioresistance to the organic or organic-containing material. The ratio of active ingredient to second salt in the kit is 10:1 to 100:1, preferably 20:1 to 90:1 and more preferably 27:1 to 70:1.

In another embodiment, the present disclosure relates to a method of treating organic or organic-containing material to waterproof and/or impart bioresistance. The method includes providing a treatment composition having an active ingredient of formula [I] as described in the present disclosure and applying the treatment composition to organic or organic-containing material. The method may also be used to prevent warping and maintain an organic or organic-containing material's as dimensional stability.

The treatment composition may be an aqueous solution. The amount of active ingredient present in the treatment composition is an amount sufficient to reduce water absorption of the organic or organic-containing material, increase dimensional stability of the organic or organic-containing material, preserve the organic or organic-containing material, or combinations thereof. The amount of active ingredient in the treatment composition is about 2 weight percent to about 70 weight percent. Preferably, the amount of active ingredient is about 5 weight percent to about 80 weight percent. More preferably, the amount of active ingredient is about 7 weight percent to about 27 weight percent.

The treatment composition may include additional ingredients such as preservatives, solvents, carriers, surfactants, buffers, etc.

The treatment composition may be applied to the organic or organic-containing material by impregnation, dipping, soaking, spraying, brushing, or other means well known in the art. For example, impregnation of the treatment composition may be carried out by the application of a vacuum/pressure process. A standard impregnation vessel may be used capable of a vacuum over a suitable period, e.g. 10-50 inch Hg from 20 minutes to 120 minutes, followed by a pressure treatment over a suitable period, e.g. 50-200 psi from form 30 minutes to 2 hours.

The method may further include the steps of providing a second treatment composition having a second salt and applying the second treatment composition to the organic or organic-containing material. The salt may be a calcium salt or a copper salt, such as calcium nitrite or copper oxide.

The amount of cation from the second salt in the second treatment composition is an amount sufficient to, in combination with the active ingredient, reduce water absorption of the organic or organic-containing material, increase dimensional stability of the organic or organic-containing material, preserve the organic or organic-containing material, or combinations thereof. The amount of cation in the second treatment composition is about 0.05 weight percent to about 2.5 weight percent. Preferably, the amount is about 0.075 weight percent to about 1.5 weight percent. More preferably, the amount is about 0.1 weight percent to about 1.0 weight percent.

The second treatment composition may include other ingredients such as water, solvents, carriers, surfactants, buffers, etc.

The second treatment composition may be applied to the organic or organic-containing material by impregnation, dipping, soaking, spraying, brushing, or other means well known in the art. The first and second treatment compositions may be applied using the same means or may be applied using different means.

In one embodiment, the first and second treatment compositions may be applied sequentially. Preferably, the active ingredient is applied first and the second salt solution is applied second. The time and pressures of the first and second treatment may vary. The time and pressures may be such that each treatment fully saturates the organic or organic-containing material. Alternatively, the treatment and treatment conditions may be such that only the organic or organic-containing material near the surface(s) is treated.

Organic or organic-containing materials, such as wood, are often used together with metal based materials, such as metal fasteners (e.g. nails or screws). The metal based materials are subject to corrosion by water. The disclosed compositions, kits and methods may protect the metal based materials from corrosion. Without wishing to be bound by any theory, it is believed that the cationic salt of a dioic acid disclosed herein is able to interact and attach to the metal based materials. By interacting and/or bonding to the metal, the dioic acid molecules form a barrier on the metal to prevent potential oxidation and associated corrosion of the metal surface.

Examples

Example 1

Pressure Treatments

The general procedures described herein were used throughout the following examples. Southern yellow pine wood obtained from a home improvement store was the test wood. The wood was cut into 6 inch×3.5 inch×¾ inch coupons. Each coupon was weighed before treatment.

A pressure treatment chamber was used to treat the wood. Metal trays held the wood samples. The solution of interest to be pressure treated into the wood was poured into the trays so that all of the wood was covered and immersed. Lead weights were used to ensure that the wood was held in position. The pressure chamber was equipped with vacuum (30 in Hg) and pressurization (150 psi air pressure) capabilities to simulate industrial wood pressure treatment.

The treatment involved applying about 30 in Hg vacuum to the samples for about 30 minutes. Thereafter, air pressure of about 145 psi was then applied for about another 60 minutes. These conditions appeared to uniformly fill the pores of the wood with the solution of interest.

For wood samples subsequently treated with a calcium solution, a second pressurization regimen was performed on the wood while still wet with the first solution. The wood to be subsequently treated was cut in half. One half was a single treatment reference. The other half was treated with the calcium solution in what is termed a dual treatment. The treatment involved applying about 30 in Hg vacuum for about 30 minutes vacuum and about 145 psi pressure for about 60 minutes.

Each coupon was weighed after the pressure treatment. Only the surface moisture was wiped off before weighing. The difference between the final and initial weights divided by the initial mass is the total weight pick up of the treatment. After pressure treatment, samples are allowed to air dry in an ambient environment for further testing.

To determine water absorption, a sample of the treated wood was cut and tested. Each sample was cut from the coupon into a cube of approximately 3×3×0.75 inches. The sample was weighed, immersed in ambient water for 5 and then 30 total minutes. After surface drying, each sample was re-weighed. The difference between the final and initial weights divided by the initial mass is the water absorption.

To determine dimensional stability, a sample of the treated wood was cut into nominally a 3 inch×3 inch×0.75 inch rectangular prism. A digital caliper was used to measure the dimensions of the sample in 3 directions to determine the volume of the sample cube. The 0.75 inch thickness dimension was measured in 4 different places and these numbers averaged to generate an average thickness. The sample was then immersed in ambient water for 30 minutes. After surface drying, the volume of each sample was re-measured. The difference in final and initial volumes divided by the initial volume is representative of the dimensional stability.

Southern Pine wood samples were pressure treated as described above. A 20% di-sodium salt of dodecenyl succinic acid (denoted C-12) in deionized water was used at 100% concentration (meaning no dilution), 50%, and 25% concentrations diluted with deionized water. Six samples were tested using each of these solutions. The difference between the final and initial weights divided by the initial mass is the total weight pick up of the treatment. (See Table 1—% total pickup). For calcium treated samples, half of the 3×3×0.75 C-12 treated wood samples were subjected to pressure treatment with a 30% calcium nitrite solution. Control samples were prepared using deionized water as a treatment solution. The results shown in Table 1 are average values, and the percentages are by mass as a fraction of the initial wood mass.

TABLE 1

Shows the results of the pressure treatments

| | Concentration C-12 Base Solution | % Total Wt Pickup | % C-12 Actives Pickup* | % Calcium Total Pickup* | % Calcium Active Pickup* |
|---|---|---|---|---|---|
| Single Treatments | | | | | |
| C-12/100 | 100% | 134% | 27% | na | na |
| C-12/50 | 50% | 135% | 13% | na | na |
| C-12/25 | 25% | 136% | 7% | na | na |
| water | 0% | 128% | 0% | na | na |
| Dual Treatments | | | | | |
| C-12/100 | 100% | 134% | 27% | 3.4% | 1.0% |
| C-12/50 | 50% | 135% | 13% | 2.0% | 0.3% |
| C-12/25 | 25% | 136% | 7% | 1.4% | 0.1% |
| water | na | 128% | na | 4.2% | 1.3% |

*Table values calculated using molecular weights of C-12, Calcium and/or water.

Example 2

Water Absorption Testing

Water absorption tests were performed on the treated wood samples prepared by the procedure described in Example 1.

Mass measurements were made after 5 and 30 minutes of water immersion. Samples were removed from the water and any droplets on the surface were removed by a damp rag. The difference between the final and initial weights divided by the initial mass is the water absorption. (See Table 2—% water mass gain). The results shown in Table 2 are average values of two replicates.

Untreated wood from the same stock was run as a control. For comparison, a generic commercial wood product known to be treated with ACQ (alkaline copper quaternary) preservative and a water repellent (ACQ-WR), and a commercial wood product named WeatherShield™ were also tested for water absorption.

TABLE 2

Shows the results of the water absorption and dimensional stability tests

|  | % water mass gain 5 minutes | % water mass gain 30 minutes | % volume gain 30 minutes |
|---|---|---|---|
| Single Treatments | | | |
| C-12/100 | 1.4% | 2.6% | 0.39% |
| C-12/50 | 2.6% | 4.5% | 0.38% |
| C-12/25 | 10.2% | 12.3% | 0.11% |
| water | 18.5% | 29.3% | 1.89% |
| Dual Treatments | | | |
| C-12/100 + Ca | 1.5% | 2.8% | 0.0% |
| C-12/50 + Ca | 2.0% | 4.1% | 0.15% |
| C-12/25 + Ca | 4.3% | 6.7% | 0.42% |
| Water + Ca | 13.7% | 23.3% | 0.64% |
| Commercial Treatments | | | |
| ACQ-WR | 2.8% | 4.5% | 0.54% |
| Weather Shield | 5.5% | 8.7% | 1.58% |
| Untreated | 9.0% | 12.0% | 1.25% |

As shown in Table 2, treatment using the cationic salt of a dioic acid provided superior hydrophobicity as compared to the control water sample as well as commercially available products. Treatment using both the cationic salt of a dioic acid and the second salt provided even greater hydrophobicity as compared to the dioic acid alone.

Example 3

Dimensional Stability Testing

Dimensional Stability tests were performed on the treated wood samples prepared by the procedure described in Example 1. Volume measurements were made 30 minutes of water immersion. Samples were removed from the water and any droplets on the surface were removed by a damp rag. The length measurements were made by electronic caliper. A single length measurement was made for the two larger dimensions. Four measurements taken at difference points were made for the smallest dimension, and then averaged. The three length measurements were multiplied to determine the volume. The difference between the final and initial volume divided by the initial volume is the dimensional stability. (See Table 2—% volume gain). As shown in Table 2, treatment using the cationic salt of a dioic acid provided superior dimensional stability as compared to the control water sample as well as commercially available products. Treatment using both the cationic salt of a dioic acid and second salt provided even greater dimensional stability as compared to the dioic acid alone.

Example 4

Bioresistance—Termites

Bioresistance tests were performed on the treated wood samples prepared by the procedure described in Example 1. Each sample was tested for termite degradation as measured by the American Wood Protection Association (AWPA) Standard Method E1-09. Samples were cut to 1×1×¾ inch specimens. Termites were allowed to consume the wood for 28 days in a controlled environment.

Untreated pine and locally obtained ACQ treated (non-waterproofed) wood samples were used as comparatives for the termite bioresistance testing. For ACQ treated wood, both treated wood suitable for above grade applications and treated wood suitable for below grade applications were tested. The below grade application wood contains high levels of ACQ and is expected to be more termite resistant.

Standard Method E1-09 provides two evaluations, a percent weight loss and a visual inspection. Both evaluations were performed. The percent sample weight loss was measured by the difference in the initial and final oven dried weight of the termite exposed sample divided by the initial weight. The AWPA visual rating system assigned a descriptor to each sample after visual inspection: 10—sound, surface nibbles permitted; 9—light attack; 7—moderate attack, penetration; 4—heavy attack and 0—failure. (See Table 3)

TABLE 3

Shows the results of the bioresistance test - termites

|  | % weight loss under E1 | E1 numerical rating |
|---|---|---|
| Single Treatment | | |
| C-12/100 | 4.42% | 10 |
| C-12/50 | 3.75% | 9 |
| C-12/25 | 6.79% | 7 |
| water | 62.02% | 0 |
| Dual Treatments | | |
| C-12/50 + Ca | 4.50% | 9 |
| C-12/25 + Ca | 3.81% | 9 |
| Water + Ca | 3.01% | 9 |
| Commercial Treatments | | |
| ACQ-Above | 5.54% | 9 |
| ACQ-Below | 1.24% | 10 |
| Untreated | 49.96% | 0 |

As shown in Table 3, treatment using the cationic salt of a dioic acid provided superior bioresistance as compared to the control water sample. Treatment using both the cationic salt of a dioic acid and second salt provided even greater dimensional stability as compared to the dioic acid alone. Both treatments are more environmentally friendly than the commercially available ACQ based treatments.

Example 5

Bioresistance—Fungal

Bioresistance tests were performed on the treated wood samples prepared by the procedure described in Example 1. Each sample was tested for fungal degradation as measured by AWPA Standard Method E22-09. Brown rot fungi were allowed to consume the wood for 30 days in a controlled environment.

Untreated pine and locally obtained ACQ treated (non-waterproofed) wood samples were used as comparatives for the fungal bioresistance testing. For ACQ treated wood, both treated wood suitable for above grade applications and treated wood suitable for below grade applications were tested.

Standard Method E22-09 provides two compressive strength evaluations, a mean stress and a maximum load test. Both evaluations were performed. The mean stress (psi) and maximum load (lbs) values were determined using an Instron™ compressive strength machine. The higher the stress or load values the less damage from fungal rot. (See Table 4)

TABLE 4

Shows the results of the bioresistance test - fungal

|  | Mean Stress (psi) | Maximum Load (lbs) |
| --- | --- | --- |
| Single Treatment | | |
| C-12/100 | 231 | 35 |
| C-12/50 | 242 | 37 |
| C-12/25 | 203 | 31 |
| water | 35 | 5 |
| Dual Treatments | | |
| C-12/100 + Ca | 309 | 47 |
| C-12/50 + Ca | 223 | 42 |
| C-12/25 + Ca | 205 | 31 |
| Water + Ca | 183 | 21 |
| Commercial Treatments | | |
| ACQ-Above | 189 | 29 |
| ACQ-Below | 220 | 36 |

As shown in Tables 3 and 4, treatment using the cationic salt of a dioic acid provided superior bioresistance as compared to the control water sample. Treatment using both the cationic salt of a dioic acid and second salt provided even greater dimensional stability as compared to the dioic acid alone. Both treatments are more environmentally friendly than the commercially available ACQ based treatments.

Example 6

Fasteners

To evaluate the effectiveness of this treatment with respect to inhibiting corrosion of metals (including steel screws, nails, or reinforcement bars), the treatment was evaluated for protection of steel from chloride induced rust in concrete.

Standard portland cement concretes were made at a water to cement ratio of 0.40. A second, identical mix was made from the same components, but had added the single treatment of C-12/100 at 0.5% of the weight of the portland cement.

To monitor corrosion inhibition, a modified ASTM G 109 procedure was used. In 6 inch cast concrete cubes, steel reinforcement bars were embedded in the fresh concrete at depths of 1 inch and 5 inches from the top surface. After concrete curing, a dike was built on the top surface. To the diked surface was ponded 15% sodium chloride solution in cycles of 12 weeks with 4 days wet, 3 days dry, followed by 12 weeks totally wet. These cycles were repeated over a 204 week period.

Samples subjected to this ponding regimen represent an accelerated exposure to corrosion of the metal reinforcement bars. To monitor this corrosion, electrodes are connected to the top and bottom reinforcement bars and a macrocell voltage is monitored across a resistor. In this way, corrosion current can be obtained by integration over the entire 204 week period. Through standard equations, this corrosion current can be converted into % iron lost, which is a measure of the extent of corrosion.

Results from this experiment are shown in Table 5.

TABLE 5

Iron Loss Results from Accelerated Corrosion Testing

|  | Dosage Level of C-12/100 (wt % of cement) | % Iron loss over 204 weeks |
| --- | --- | --- |
| Single Treatment C-12/100 | 0.5% | 0.01% |
| Untreated Control | 0 | 0.148% |

As shown in Table 5, treatment using the cationic salt of a dioic acid is able to inhibit the corrosion of the metal reinforcement bar.

While the present invention has been described with respect to the exemplary embodiments thereof, it will be recognized by those of ordinary skill in the art that many modifications, enhancements, variations and/or changes can be achieved without departing from the spirit and scope of the invention. Therefore, it is manifestly intended that the invention be limited only by the scope of the claims and equivalents thereof.

What is claimed is:

1. A kit comprising:
   (i) a first component being an active ingredient of formula [I]

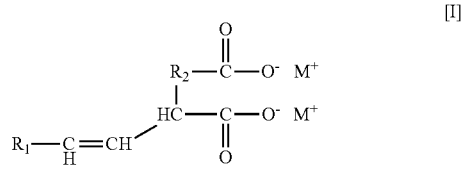

wherein $R_1$ is an aliphatic hydrocarbon, $R_2$ is a $C_1$ to $C_{10}$ hydrocarbon, and each $M^+$ is independently a cation, and wherein the active ingredient has a blend or mixture of molecules having differing R1 structures, and
   (ii) a second component being a calcium or copper salt.

2. The kit of claim 1, wherein the blend or mixture of $R_1$ defines a weight average, and wherein the weight average of the blend or mixture of $R_1$ is about a $C_6$ to $C_{16}$ hydrocarbon.

3. The kit of claim 1, wherein the blend or mixture of $R_1$ defines a weight average, and wherein the weight average of the blend or mixture of $R_1$ is about a $C_{12}$ hydrocarbon.

4. The kit of claim 1, wherein the blend or mixture of $R_1$ defines a weight average, and wherein the weight average of the blend or mixture of $R_1$ is about a $C_{12}$ hydrocarbon and $R_2$ is a $C_1$ hydrocarbon.

5. The kit of claim 1, wherein $R_1$ is branched.

6. The kit of claim 1, wherein each $M^+$ is independently sodium, potassium or lithium.

7. The kit of claim 1, wherein the first component comprises between about 0.1 and 50 weight percent active ingredient.

8. The kit of claim 1, wherein the first component comprises between about 0.01 and 10 weight percent of the cation from the second component.

9. The kit of claim 1, wherein the active ingredient is effective to reduce water absorption of an organic or organic-containing material selected from the group consisting of wood, textile fiber and combinations thereof.

10. The kit of claim 1, wherein the active ingredient is present in an amount sufficient to reduce water absorption of an organic material, increase dimensional stability of the organic material, preserve the organic material, or combinations thereof.

11. A method of treating an organic-containing material comprising the steps of:
(i) providing a first composition having an active ingredient of formula [I]

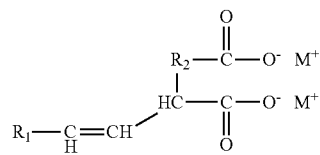

[I]

wherein $R_1$ is an aliphatic hydrocarbon, $R_2$ is a $C_1$ to $C_{10}$ hydrocarbon, each $M^+$ is independently a cation, and wherein the active ingredient has a blend or mixture of molecules having differing $R_1$ structures,
(ii) applying the first composition to the organic-containing material,
(iii) providing a second composition having a second salt, wherein the second salt is a calcium or copper salt, and
(iv) then applying the second composition to the organic-containing material.

12. The method of claim 11, wherein the first composition is applied to the organic-containing material in an amount sufficient to reduce water absorption of the organic-containing material, increase dimensional stability of the organic-containing material, preserve the organic-containing material, prevent warping of the organic-containing material, or combinations thereof.

13. The method of claim 11, wherein the organic-containing materials is a wood or a wood-containing material.

14. A product for building or construction selected from the group consisting of fencing, siding, decking, window frames, sills, doors, trim board, posts, railroad ties and telephone/electrical poles, comprising:
(i) an organic-containing material, and
(ii) an active ingredient of formula [I]

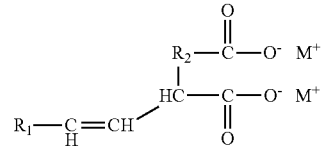

[I]

wherein $R_1$ is an aliphatic hydrocarbon, $R_2$ is a $C_1$ to $C_{10}$ hydrocarbon, and each $M^+$ is independently a cation.

15. The product of claim 14, wherein $R_1$ is a blend or mixture, and wherein the weight average of the blend or mixture of $R_1$ is about a $C_6$ to $C_{16}$ hydrocarbon.

16. The product of claim 15, wherein the weight average of the blend or mixture of $R_1$ is about a $C_{12}$ hydrocarbon.

17. The product of claim 15, wherein the weight average of the blend or mixture of $R_1$ is about a $C_{12}$ hydrocarbon and $R_2$ is a $C_1$ hydrocarbon.

18. The product of claim 14, wherein $R_1$ is branched.

19. The product of claim 14, wherein each $M^+$ is independently sodium, potassium or lithium.

20. The product of claim 14, wherein the active ingredient is effective to reduce water absorption of the organic-containing material which is selected from the group consisting of wood, textile fiber and combinations thereof.

21. The product of claim 14, wherein the active ingredient is present in an amount sufficient to reduce water absorption of the organic-containing material, increase dimensional stability of the organic-containing material, preserve the organic-containing material, or combinations thereof.

* * * * *